US008409372B1

(12) United States Patent
Padula, II

(10) Patent No.: US 8,409,372 B1
(45) Date of Patent: Apr. 2, 2013

(54) THERMOMECHANICAL METHODOLOGY FOR STABILIZING SHAPE MEMORY ALLOY (SMA) RESPONSE

(75) Inventor: Santo A Padula, II, Valley City, OH (US)

(73) Assignee: The United States of America as Represented by the Administraton of National Aeronautics and Space Administration, Washington, DC (US)

( * ) Notice: Subject to any disclaimer, the term of this patent is extended or adjusted under 35 U.S.C. 154(b) by 352 days.

(21) Appl. No.: 12/874,523

(22) Filed: Sep. 2, 2010

(51) Int. Cl.
C22F 1/00 (2006.01)
C21D 1/54 (2006.01)
C21D 1/55 (2006.01)
(52) U.S. Cl. .................................. 148/402; 148/508
(58) Field of Classification Search .............. 148/402, 148/508
See application file for complete search history.

(56) References Cited

PUBLICATIONS

Hartl et al. "Use of a Ni60Ti shape memory alloy for active jet engine chevron application: I. Thermomechanical characterization." Dec. 14, 2009.*

* cited by examiner

Primary Examiner — Keith Walker
Assistant Examiner — Alexander Polyansky
(74) Attorney, Agent, or Firm — Robert H. Earp, III

(57) ABSTRACT

Methods and apparatuses for stabilizing the strain-temperature response for a shape memory alloy are provided. To perform stabilization of a second sample of the shape memory alloy, a first sample of the shape memory alloy is selected for isobaric treatment and the second sample is selected for isothermal treatment. When applying the isobaric treatment to the first sample, a constant stress is applied to the first sample. Temperature is also cycled from a minimum temperature to a maximum temperature until a strain on the first sample stabilizes. Once the strain on the first sample stabilizes, the isothermal treatment is performed on the second sample. During isothermal treatment, different levels of stress on the second sample are applied until a strain on the second sample matches the stabilized strain on the first sample.

14 Claims, 6 Drawing Sheets

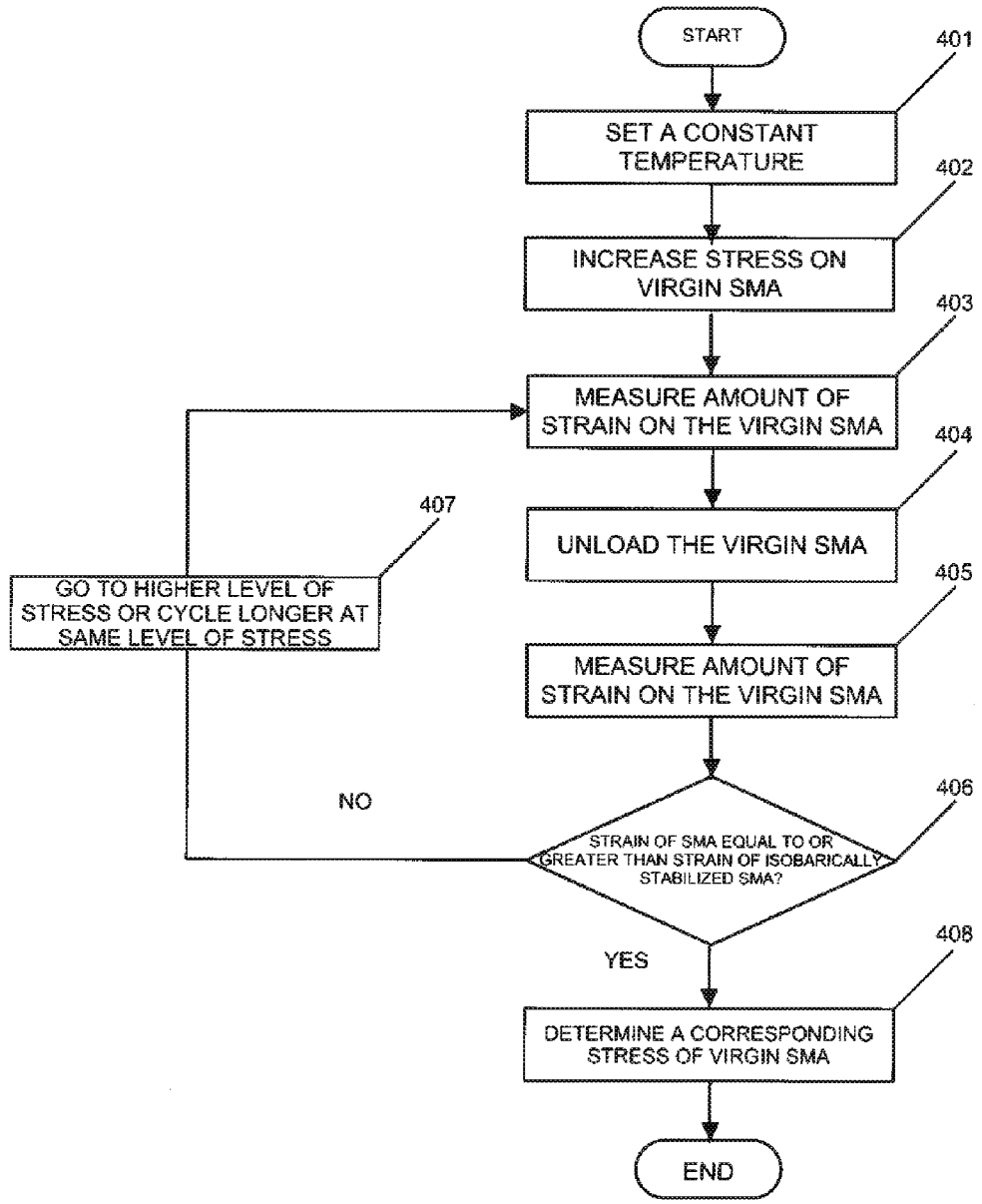

THERMOMECHANICAL METHODOLOGY FOR STABILIZING SHAPE MEMORY ALLOY (SMA) RESPONSE

ORIGIN OF THE INVENTION

The invention described herein was made by an employee of the United States Government and may be manufactured and used by or for the Government for Government purposes without the payment of any royalties thereon or therefore.

FIELD

The invention is related to stabilizing shape memory alloy (SMA) response and, more particularly, to stabilizing a strain-temperature response of the SMA.

BACKGROUND

Shape memory alloys are being developed for use as actuators, switches, and other devices in industries such as the aerospace industry and the automotive industry. An important aspect of developing SMA technology is the ability to achieve a stabilized SMA response, which includes the ability to perform movement of a mass or weight multiple times in a repeatable way. Generally, most SMAs exhibit dimensional instability when thermally cycled in the presence of applied stress. This can be thought of as "ratcheting" or "drifting" of the SMA during its service life, which diminishes the repeatability of an SMA actuator or switch. This dimensional instability makes it difficult or impossible to design useful components with the SMA in its initial processed condition because a design engineer is required to account for the dimensional changes that would occur during the service life of the SMA.

SUMMARY

In accordance with one or more embodiments of the present invention, a method of stabilizing a strain-temperature response for a shape memory alloy is performed. The method includes selecting a first sample of the shape memory alloy for isobaric treatment and a second sample of the shape memory alloy for isothermal treatment, in order to train the shape memory alloy. When applying the isobaric treatment to the first sample, a constant stress is applied to the first sample and temperature is cycled from a minimum temperature to a maximum temperature until strain on the first sample stabilizes. When applying the isothermal treatment to the second sample, different levels of stress can be applied on the second sample until strain on the second sample matches the stabilized strain on the first sample.

Also in accordance with one or more embodiments of the present invention, an additional method of stabilizing a strain-temperature response for a shape memory alloy can be performed. The method includes selecting a first sample of the shape memory alloy for isobaric treatment and a second sample of a shape memory alloy for isothermal treatment, in order to train and stabilize the shape memory alloy against the isobaric condition. When applying the isobaric treatment to the first sample, a constant stress is applied to the first sample and temperature is cycled from a minimum temperature to a maximum temperature until the strain within the first sample stabilizes. When applying the isothermal treatment to the second sample, applying a stress to the second sample until the second sample fails, measuring each strain within the second sample according to different levels of stress applied on the second sample, and matching a strain from the measured strains of the second sample with the stabilized strain of the first sample In yet other embodiments of the present invention, an apparatus is configured to stabilize a strain-temperature response for a shape memory alloy. The apparatus includes a pressure unit configured to apply stress and a temperature unit configured to supply a stable temperature or cycle temperature from a minimum temperature to a maximum temperature. When applying the isobaric treatment to a first sample of the shape memory alloy, the pressure unit is configured to apply a constant stress to the first sample. Also, the temperature unit is configured to cycle temperature from a minimum temperature to a maximum temperature until strain on the first sample stabilizes. When applying the isothermal treatment to the second sample, the pressure unit can further be configured to apply different levels of stress on the second sample until strain on the second sample matches the stabilized strain on the first sample.

BRIEF DESCRIPTION OF THE DRAWINGS

For a proper understanding of the invention, reference should be made to the accompanying figures. These figures depict only some embodiments of the invention and are not limiting of the scope of the invention. Regarding the figures:

FIG. 4 illustrates a method for performing isothermal mechanical cycling to a virgin sample of a SMA, in accordance with one or more embodiments of the present invention;

DETAILED DESCRIPTION OF THE EMBODIMENTS

It will be readily understood that the components of the invention, as generally described and illustrated in the figures herein, may be arranged and designed in a wide variety of different configurations. Thus, the following detailed description of the embodiments is not intended to limit the scope of the invention as claimed, but is merely representative of selected embodiments of the invention.

The features, structures, or characteristics of the invention described throughout this specification may be combined in any suitable manner in one or more embodiments. For example, the usage of "certain embodiments," "some embodiments," or other similar language, throughout this specification refers to the fact that a particular feature, structure, or characteristic described in connection with an embodiment may be included in at least one embodiment of the invention. Thus, appearances of the phrases "in certain embodiments," "in some embodiments," "in other embodiments," or other similar language, throughout this specification do not necessarily all refer to the same embodiment or group of embodiments, and the described features, structures, or characteristics may be combined in any suitable manner in one or more embodiments.

In one embodiment of the present invention, a method and an apparatus may be configured to establish a stabilization point for a SMA (i.e., the absolute strain achieved after stabilization) by performing an isobaric experiment to a sample of the SMA under conditions identical to those that will be used during the service life of the SMA. The isobaric experiment may be called an isobaric treatment or condition. Once the stabilization point is known, a set of isothermal mechanical cycling experiments are performed on a virgin sample of the SMA material using different levels of applied stress. The mechanical cycling experiments are performed until the strain on the virgin sample has reached the same stabilized strain that was assessed under the isobaric experiment.

In other embodiments, the process is performed by a single isothermal loading to achieve stabilization. For example, a sufficiently high stress or load is applied to the virgin sample of the SMA material until the material breaks, fractures, buckles or bulges (depending on the mode of loading). As a result, the strain within the virgin sample at different stresses can be determined and compared with the strain within the isobarically trained sample.

Once the stress under isothermal conditions (required to achieve stabilization under isobaric conditions) is known, the stress can be utilized to train other virgin pieces or the remaining SMA material for the isobaric condition in a fraction of the time. Hence, once the strain state is achieved isothermally, the trained SMA can be switched back under isobaric conditions and will remain stabilized for the remainder of its service life.

Figure 1:
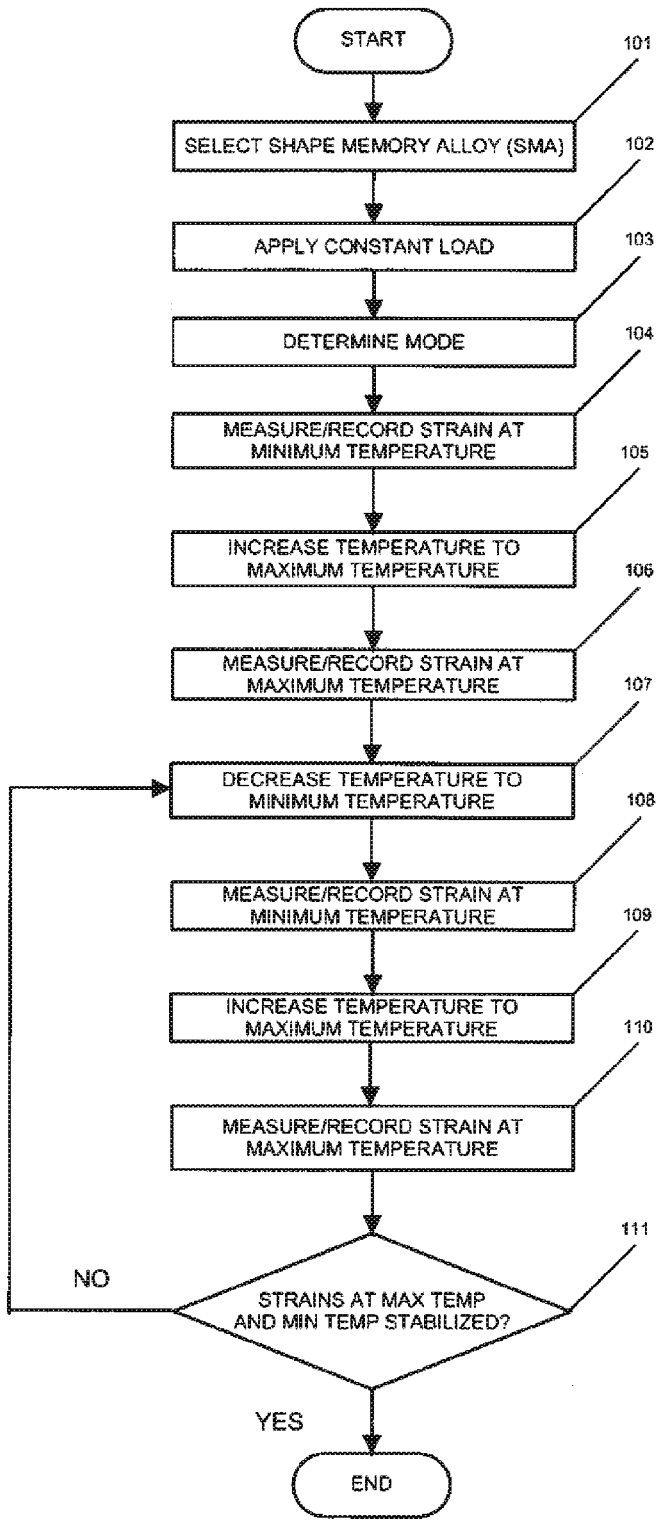
FIG. 1 illustrates a method for performing an isobaric treatment to a sample of a SMA, in accordance with one or more embodiments of the present invention.

FIG. 1 illustrates a method for performing an isobaric treatment to a sample of a SMA, in accordance with one or more embodiments of the present invention. When performing the isobaric treatment, a sample of the SMA is placed under an intended service condition (or service stress) and then continuously thermally cycled until a stable performance is realized, i.e., strain points on the sample are consistent.

To begin, a sample of the SMA is selected at 101, which may be formed into a wire, a tube, or any other suitable structure. For example, the wire, tube, or structure may comprise any of the following: Ag—Cd, Au—Cd, Cu—Al—Ni, Cu—Sn, Cu—Zn, Fe—Pt, Mn—Cu, Fe—Mn—Si, Pt alloys, Co—Ni—Al, Co—Ni—Ga, Ni—Fe—Ga, Ti—Pd, Ni—Ti, Ni—Ti—X, or Ni—Mn—Ga. In certain embodiments, the letter "X" in Ni—Ti—X can be any one of the following: platinum, palladium, gold, hafnium, as well as other types of ternary and quaternary alloys, or any combination thereof. However, it is understood that this list is offered by way of example only and other alloys may be used.

At 102, an external stress in the form of a constant load or stress is applied to the sample. At 103, a determination is made as to whether the external stress applied to the sample is in a tension mode, a compression mode, or a torsion mode. Tension, compression, and torsion are known as "pure modes". In other embodiments, the stress can be applied to the sample in a combination of tension, compression and torsion (e.g., multi-axial stress).

Depending on the mode, contraction versus extension can be different. For example, in the compression mode, when a load is applied to the sample, the sample may compress in a martensite state and extend in an austenite state. However, in the tension mode, when the load is applied to the sample, the sample may extend in the martensite state and contract in the austenite state. In the torsion mode (similar to sheer), for example, the sample may operate between two different positions depending on the applied external stress. The strain at each position can be measured in a similar fashion by, for example, a torsion extensometer.

At 103, if the mode is determined to be tension, then application of the load or stress in the martensite state causes the sample to be deformed (i.e. extended or elongated). Deformation is any mechanical loading that creates strain in the sample of the SMA material. The constant load can be based on the intended service load of the SMA and can be dependent upon the size of the SMA. A suitable pressure unit, such as a hydraulic test frame or hydraulic piston, can be used to apply the load.

Furthermore, in certain embodiments, maximum and minimum temperatures and stresses can be dictated by the intended application conditions or service conditions, i.e., the loads/stress and the temperatures that the actuator may see in service. In this embodiment, any temperature that allows the material to remain in the martensite state is regarded as a minimum temp or $TEMP_{min}$. At 104, strain asserted on the sample in the martensite state is determined or measured and recorded. A measuring unit, such as an extensometer or an extension gauge, can be configured to determine the strain asserted on the sample in the martensite state and austenite state. The recorded strain may be called the strain within the martensite state 1, or $\epsilon M_1$.

By utilizing heating and cooling processes or a temperature unit such as an induction heater, a resistance furnace, a tape heater or resistance (joule) heating, the temperature that the sample experiences can be changed. For example, at 105, the temperature is increased to a maximum temperature or $TEMP_{max}$, causing the sample to decrease or contract in size (tension mode). At this point, the sample is considered to be in the austenite state. At 106, strain asserted on the sample in the austenite state is measured and recorded. The recorded strain may be called the strain at austenite state 1, or $\epsilon_{A1}$.

At 107, the sample is cooled to $TEMP_{min}$, causing the sample to extend. The cooled sample may extend to be longer than the originally deformed sample. At this point, the cooled sample is in the martensite state. At 108, strain asserted on the sample in the martensite state is measured and recorded. The recorded strain may be called the strain at $\epsilon_{M2}$. However, the strain at $\epsilon_{M2}$ and the strain at $\epsilon_{M1}$ may not be equivalent because the strain in the martensite state has not stabilized.

At 109, the sample is heated to $TEMP_{max}$, causing the sample to decrease or contract in size. At this point, the sample is in the austenite state. At 110, the strain asserted on the sample in the austenite state is measured and recorded. The recorded strain may be called the strain at $\epsilon_{A2}$. Because the contracted sample can undergo a smaller contraction than pervious contractions, the strain at $\epsilon_{A2}$ may not be equivalent to the strain at $\epsilon_{A1}$.

At 111, previously recorded strains in the martensite and austenite states are compared to determine whether the strains have stabilized (i.e., are consistent from cycle to cycle). For example, a determining unit or a controller can be configured to compare and determine whether the strains have stabilized. If the strains within the martensite and austenite states have not stabilized, then steps 107 to 110 are repeated until the recorded strains within the martensite and austenite states have stabilized.

For example, during the first cycle, at room temperature, the strain on the sample is at position $\epsilon_{M1}$ and, when the temperature is increased to 165° C. (i.e., a possible $TEMP_{max}$ for a typical binary Ni—Ti), the strain on the sample is at position $\epsilon_{A1}$. On the next cycle, when the temperature is lowered to room temperature (i.e., a possible TEMP$_{min}$ for binary Ni—Ti), the strain on the sample is at position $\epsilon_{M1}$ and, when the temperature is increased again to 165° C., the strain on the sample is at $\epsilon_{A2}$. In other words, the cycle of increasing and decreasing the temperature from TEMP$_{min}$ to TEMP$_{max}$ is performed N times until the strain on the sample at $\epsilon_{mN}$ and the strain on the sample at $\epsilon_{AN}$ have stabilized. Upon stabilization, the strain in the martensite state is known for the selected sample. While the method of FIG. 1 is capable of determining the stabilization point of the strain in the martensite state, the stabilization point of the strain in the austenite state can be determined as well.

If the mode at 103 is determined to be compression, then the constant load or stress being applied to the sample can cause the sample to be compressed in the martensite state. At 104, the strain in the martensite state is measured and recorded. When the sample is heated or temperature is increased to a maximum temperature at 105, the sample extends against the stress in an attempt to recover the original shape, i.e., the austenite state. At 106, the strain in the austenite state may then be measured and recorded. When the sample is cooled to the martensite state at 107, the sample compresses in the presence of the applied stress, i.e., the deformed state. At 108, the strain in the martensite state is measured and recorded again. When the sample is heated at 109, the sample extends to the austenite state. At 110, the strain in the austenite state is measured and recorded again. At 111, a determination is made as to whether the recorded strains in the martensite and austenite states have stabilized. If the recorded strains in the martensite and austenite states have stabilized, then the process is complete. If the recorded strains in the martensite and austenite states have not stabilized, then steps 107 to 110 are repeated N times until the strains in the martensitic and austenite states have stabilized.

If the mode is determined at 103 to be torsion, then the constant torque or stress being applied to the sample causes the sample to be twisted in the martensite state. For example, when the sample is fixed at one end and a constant stress/torque is applied at the other end of the sample, the sample is deformed. At 104, the strain in the martensite state is measured and recorded.

When the sample is heated and cooled, the sample can rotate between two different positions against the torque. For example, when the sample is heated at 105, the sample can rotate to the austenite state, i.e., toward the un-torqued state. At 106, the strain in the austenite state is then measured and recorded. When the sample is cooled at 107, the sample can rotate to the deformed martensitic state. At 108, the strain in the martensite state is then measured and recorded. The sample is then heated again at 109, and the strain in the austenite state is measured and recorded again at 110. At 111, a determination is made as to whether the recorded strains (or positions, commonly referred to as twist angle) in the martensite and austenite states have stabilized. If the recorded strains in the martensite and austenite states have stabilized, then the process is complete. If the recorded strains in the martensite and austenite states have not stabilized, then steps 107 to 110 may be repeated N times until the strains in the martensite and austenite states have stabilized.

Figure 2:
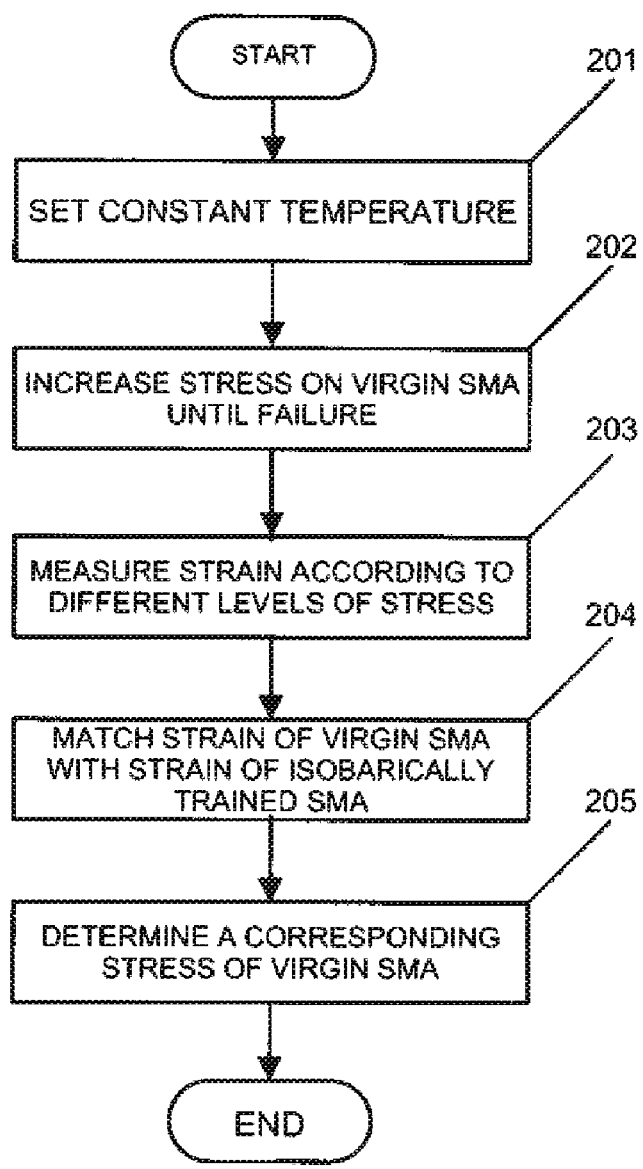
FIG. 2 illustrates a method for performing isothermal mechanical loading to a virgin sample of a SMA, in accordance with one or more embodiments of the present invention.
Figure 6:
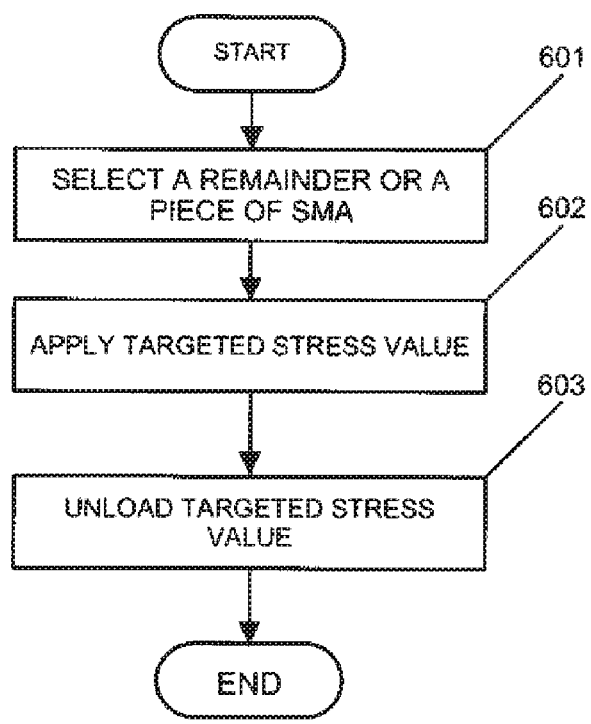
FIG. 6 illustrates a method of performing isothermal treatment on an object comprising the SMA, in accordance with one or more embodiments of the present invention.

Stated another way, the embodiments of FIG. 1 provide isobaric treatment to the sample of the SMA so a stabilized strain response of the SMA in the martensite state can be determined. For example, under isobaric treatment, a load-bias response of 55Ni—Ti, when cycling at 100 MPa between room temperature (RT) and 165 Degrees Celsius, yields a stabilized strain of around 14%. The stabilized strain enables isothermal mechanical cycling or loading to be performed on a virgin sample of the SMA, as shown in FIGS. 2 and 4. The isothermal mechanical cycling or loading for a determination to be made as to what stress level the SMA would need to see in order to achieve a similar level of strain as was determined under the isobaric conditions. Once the stress level for the SMA is determined, the determined stress level, as shown in FIG. 6, can be applied to a piece of or remaining SMA so as to achieve a strain in the SMA that will stabilize the SMA against the isobaric service conditions of interest more quickly and efficiently.

FIG. 2 illustrates a method for performing isothermal mechanical loading to a virgin sample of a SMA, in accordance with one or more embodiments of the present invention. Stated another way, FIG. 2 shows a method of reducing the isothermal mechanical cycling experiment to a single process. In this embodiment, at 201, a temperature is set to a constant, the constant temperature being the same as TEMP$_{min}$ described in reference to FIG. 1. As the temperature remains constant, a large or sufficient amount of stress at 202 is applied on the virgin sample of the SMA until failure. In this embodiment, depending on the mode of loading, failure can be breaking, fracturing, buckling or bulging. At 203, a plurality of strains are measured and recorded according to different amounts of stress being applied on the virgin sample. At 204, from the plurality of measured strains recorded during the isothermal test, a strain that matches the strain of the isobarically trained sample of the SMA is determined. At 205, once the strain of the isobarically trained sample is matched with an equivalent strain of the virgin sample in the isothermal monotonic response, a stress level corresponding to the matched strain is determined. This corresponding stress level can now be used to train other virgin pieces or the remaining SMA using an isothermal treatment, as shown in FIG. 6.

Stated another way, the isobaric stabilization strain is matched to the corresponding isothermal monotonic response strain. The isothermal monotonic response strain determines the amount of loading required in the isothermal state in order to achieve a strain state that would stabilize the virgin sample for the service conditions of interest. Once the required loading amount is determined, then the method of training other virgin pieces or the remaining SMA using an isothermal treatment can be achieved quicker and more efficiently. As a result, such embodiments can significantly reduce the amount of time required to stabilize strain temperature response of the SMA. In addition, such embodiments not only reduce the cost, but also improve viability of utilizing SMA based technologies in products requiring more efficient, compact, and lightweight actuation solutions.

Figure 3:
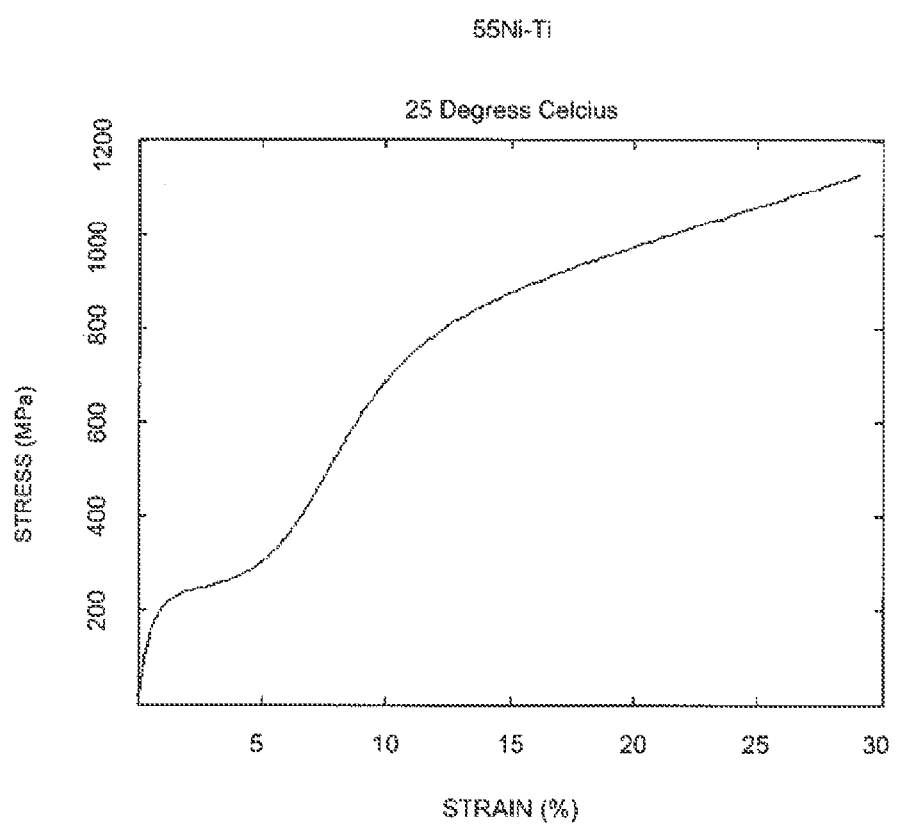
FIG. 3 illustrates a graph showing results of isothermal mechanical loading to a virgin sample of a SMA, in accordance with some embodiments of the present invention.

FIG. 3 illustrates a graph showing results of isothermal mechanical loading to a virgin sample of a SMA, in accordance with some embodiments of the present invention. In this embodiment, the virgin sample of the SMA (e.g. 55Ni—Ti) at 25° C. is incrementally loaded while the corresponding strain within the sample is measured (via a strain gauge or an extensometer device). The stress on the sample is increased continuously until the sample fails (breaks, bulges or buckles, depending on the mode of loading). Subsequent to the failure of the sample, the isothermal, monotonic stress/strain response can be utilized to determine the amount of stress required to achieve a strain in the SMA that will stabilize the SMA against the isobaric service conditions of interest. Care, however, should be taken when choosing the stress, as the shape of the unloading curve of the stress/strain response cannot be determined from this test. Therefore, slightly higher stresses than those retrieved directly from the graph can be used to account for the strain recovery, which can occur during the unloading phase of the isothermal, mechanical training process.

FIG. 4 illustrates a method of performing isothermal mechanical cycling to a virgin sample of a SMA, in accordance with some embodiments of the present invention. In this embodiment, a set of isothermal mechanical cycling experiments is performed on the virgin sample of the SMA by applying different levels of stress. In other words, the set of isothermal mechanical cycling experiments is performed until the strain of the isothermally cycled, virgin sample of the SMA is equal to or greater than the strain within the isobarically trained sample of the SMA from FIG. 1.

At 401, a constant temperature is set. For example, in some embodiments, the constant temperature is the same as $TEMP_{min}$ discussed in reference to FIG. 1, which was used to determine the stabilized strain for the martensite state of the isobarically trained sample. However, in other embodiments, the constant temperature can be set to any temperature between $TEMP_{min}$ and $TEMP_{max}$ as long as the temperature remains constant. From 402 to 406, the virgin sample is mechanically cycled by applying different amounts of stress until the strain in the virgin sample, when unloaded, is equal to or greater than the strain of the isobarically trained SMA discussed in reference to FIG. 1. Steps 402 to 406 are discussed in greater detail below.

At 402, a predetermined amount of stress is applied on the virgin sample with the temperature remaining constant and a corresponding strain is recorded at 403. In some embodiments, a hydraulic test frame, a hydraulic piston, or any suitable equipment capable of producing a thermomechanical loading of the virgin sample may be used. For example, to isothermally, mechanically train the virgin sample for an actuator condition, any type of structure or pressure unit may be used to increase the load or stress on the virgin sample and control the amount of deformation placed into the virgin sample.

At 404, the predetermined stress on the virgin sample is removed or unloaded (i.e. stress is reduced to zero) and the corresponding strain is measured/recorded at 405. At 406, the strain on the virgin sample, when the stress has been removed, is compared to the stabilized strain of the isobarically treated (trained) sample from FIG. 1. This comparison can be performed by a determining unit, which can be any type of computer processing equipment. If the strain on the virgin sample is not equal to or greater than the stabilized strain of the isobarically trained sample, then, depending on conditions, a higher level of stress is applied or the stress is cycled longer at the same level at 407, and steps 403 to 406 are repeated. If the strain on the virgin sample is equal to or slightly greater than the stabilized strain of the isobarically trained sample, then at 408 a stress level corresponding to the equivalent strain is determined. This corresponding stress level can now be used to train other pieces or the remaining SMA under an isothermal treatment, as shown in FIG. 6.

Stated another way. FIG. 4 shows a set of isothermal mechanical cycling experiments being performed using different levels of applied stress. Each of these mechanical cycling experiments is performed until the strain response has stabilized. Successive stress levels are investigated until the virgin sample has reached the same stabilization point that was assessed under the isobaric experiment. As a result, this embodiment can significantly reduce the amount of time required to stabilize the strain-temperature response of the virgin sample by using mechanical cycling to reach the strain stabilization point. In particular, unlike traditional stabilization processes, which take days or weeks to achieve a stabilized response, this embodiment can accomplish stabilization in a matter of minutes by applying mechanical cycles instead of thermal cycles.

FIGS. 5A-5D illustrate graphs showing results of isothermal mechanical cycling to a virgin sample of a SMA, in accordance with some embodiments of the present invention. For example, FIGS. 5A-5D show differences in behavior by mechanically cycling Ni—Ti to stress amounts of 270 MPa, 290 MPa, 490 MPa, and 800 MPa, respectively. These stresses correspond to regions of monotonic stress versus strain response indicative of the middle of the detwinning plateau, the end of the detwinning plateau, the middle of the re-hardening region, and the "yield onset" region, respectively. Table 1 further illustrates attraction or saturation strains of Ni—Ti at different stress amounts.

TABLE 1

Mechanical Attraction Points for Ni-Ti

| Test Temperature (° C.) | Presumed Material State | Lower Stress (MPa) | Upper Stress (MPa) | $\epsilon_M^0$ (%) | $\epsilon_M^\sigma$ (%) |
|---|---|---|---|---|---|
| RT | Martensite | 0 | 270 | 2.26 | 2.83 |
| RT | Martensite | 0 | 290 | 3.35 | 4.02 |
| RT | Martensite | 0 | 490 | 6.07 | 7.13 |
| RT | Martensite | 0 | 800 | 13.42 | 16.23 |

However, before results from the graphs shown in FIGS. 5A-5D and Table 1 can be understood, a brief discussion of determining a stabilized strain of Ni—Ti under isobaric treatment is provided. In this embodiment, before an isothermal mechanical cycling experiment or treatment on Ni—Ti can be performed, an isobaric treatment is conducted to determine a stabilized saturation strain or attraction of Ni—Ti. For example, the isobaric treatment of Ni—Ti can be performed via the method shown in FIG. 1. In particular, a load-bias response of Ni—Ti (55NiTi, $A_s$~95° C.) when cycling at 100 MPa between room temperature (RT) and 165 Degrees Celsius, after starting from a "self-accommodated" state, yields resultant strain values of $\epsilon_M^{100}$~14% and $\epsilon_A^{100}$~11%, respectively. $\epsilon_M^{100}$ is a strain value of Ni—Ti with 100 MPa of stress at a low temperature state (e.g., martensitic state or daughter state) and $\epsilon_M^{100}$ is a strain value of Ni—Ti with 100 MPa of stress at a high temperature state (e.g., austenitic state or parent state). By determining the strain value of Ni—Ti with 100 MPa at room temperature, the isothermal mechanical cycling treatment can be performed with stress values shown in FIGS. 5A-5D.

Figure 5A:
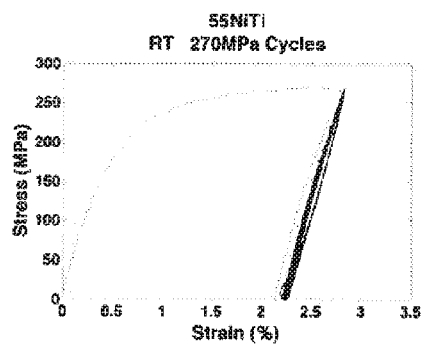
FIGS. 5A-5D illustrate graphs showing results of isothermal mechanical cycling to a virgin sample of a SMA, in accordance with some embodiments of the present invention.
Figure 5B:
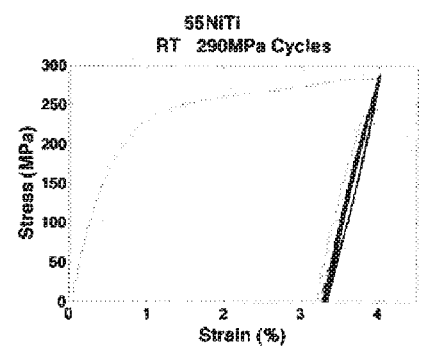
Figure 5C:
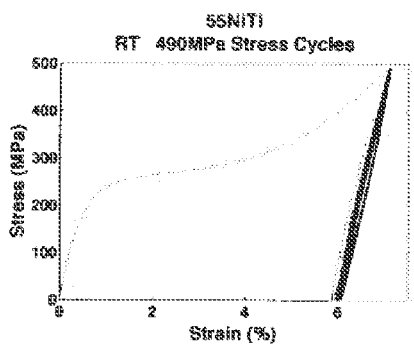

In FIG. 5A, when 270 MPa of stress is applied to Ni—Ti, an isothermal stabilization strain of 2.83% is realized. When the stress is unloaded or at a lower stress, a strain of 2.26% is realized. However, the strain of 2.26% is not enough to train or prepare Ni—Ti for the isobaric conditions (e.g. 100 MPa of stress which requires around ~14% strain in tension). As a result, the stress level applied to Ni—Ti under isothermal mechanical cycling is increased. For example, FIG. 5B shows 290 MPa of stress being applied to Ni—Ti causing a strain of 4.02%.

Figure 5D:
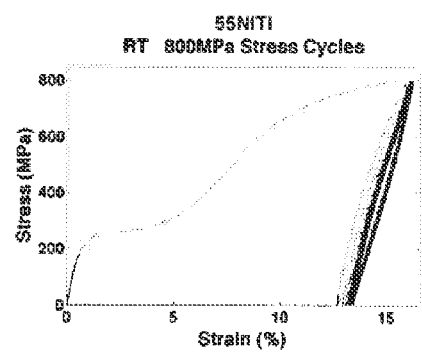

However, after unloading the 290 MPa of stress, a strain of 3.35% is realized. Because the strain, after unloading the stress of 290 MPa, is not close to or equal to the strain value of $\epsilon_M^{100}$~14%, a higher amount of stress is applied (see FIG. 5C). Similar to the results shown in FIGS. 5A and 5B, the strain of Ni—Ti, after unloading a stress of 490 MPa, is not close to or equal to the strain value of $\epsilon_M^{100}$~14%. As a result, stress is increased to 800 MPa as shown in FIG. 5D and Table 1. In particular, FIG. 5D shows that after unloading Ni—Ti that has been cycled to a stress of 800 MPa for a number of cycles, the strain within the material is close to or equal to the strain value of $\epsilon_M^{100}$~14%. See also Table 1.

Therefore, as shown in FIGS. 5A-5D, Ni—Ti quickly reaches saturation for each of the conditions with observed ending strain being represented by $\epsilon_M^0$ (at zero stress) and $\epsilon_M^0$ at the upper stress used for the mechanical cycling. Moreover, Table 1 shows the values for each of these strains for conditions where the mechanical open-loop strain ($OLS_M$) had reached a value on the order of <0.005%. Thus, in this embodiment, 800 MPa of stress is sufficient to train Ni—Ti via isothermal mechanical cycling for a given isobaric condition close to 100 MPa.

FIG. 6 illustrates a method of performing isothermal treatment on an object comprised of the SMA, in accordance with one or more embodiments of the present invention. The depicted method generally describes training remaining or a piece of the SMA after determining the amount of stress required to produce a stabilized strain, as shown in FIGS. 2 and 4. At 601, an object comprised of a piece or remaining SMA is selected to be trained under the isothermal treatment. At 602, a targeted stress value is applied to the piece or the remainder of the SMA. The targeted stress value is based on the stress value determined from FIGS. 2 and 4, i.e., the stress value to achieve a stabilized strain. At 603, the targeted stress value is unloaded from the piece or the remainder of the SMA. As a result, a single loading and unloading of the targeted stress value can be used to stabilize the strain response of the piece or the remainder of the SMA, for the isobaric condition of interest.

The method steps performed in FIGS. 1, 2, 4, and 6 may be performed, in part, by a computer program product, encoding instructions for a nonlinear adaptive processor to cause at least the methods described in FIGS. 1, 2, 4, and 6 to be performed by the apparatuses discussed herein. The computer program product may be embodied on a computer readable medium. The computer readable medium may be, but is not limited to, a hard disk drive, a flash device, a random access memory, a tape, or any other such medium used to store data. The computer program product may include encoded instructions for controlling the nonlinear adaptive processor to implement the method described in FIGS. 1, 2, 4, and 6, which may also be stored on the computer readable medium.

The computer program product can be implemented in hardware, software, or a hybrid implementation. The computer program product can be composed of modules that are in operative communication with one another, and which are designed to pass information or instructions to display. The computer program product can be configured to operate on a general purpose computer, or an application specific integrated circuit ("ASIC").

In other embodiments, a thermomechanical processing methodology is based on a generalized theory known as attraction law theory. Under this theory, the SMA material is "attracted" to a strain-state based on a combination of an applied stress and a temperature condition. The advantages of such embodiments may include reducing the amount of time required to achieve a stabilized material response (under multi-axial conditions) from times on the order of days or weeks down to a matter of minutes. This is achieved by performing an isobaric experiment on a sample of the SMA under conditions identical to those that will be used during the service life of the SMA or any structure comprised of an SMA. The isobaric experiment establishes a stabilization point for the SMA or SMA-based structure. Once known, a set of isothermal mechanical experiments is performed using different levels of applied stress on a virgin sample of the SMA or structure. Successive stress levels are investigated until the virgin sample has reached the same stabilization point that was assessed under the isobaric condition. Once the strain state is achieved isothermally, the virgin sample can be switched back under isobaric conditions and will remain stabilized for the remainder of the service life. This embodiment is a target approach to achieve the deformation on the SMA component that is needed to get stabilization and optimizes the ability to maintain optimal lifing of the component.

One having ordinary skill in the art will readily understand that the invention as discussed above may be practiced with steps in a different order, and/or with hardware elements in configurations that are different than those which are disclosed. Therefore, although the invention has been described based upon these preferred embodiments, it would be apparent to those of skill in the art that certain modifications, variations, and alternative constructions would be apparent, while remaining within the spirit and scope of the invention. In order to determine the metes and bounds of the invention, therefore, reference should be made to the appended claims.

The invention claimed is:

1. A method of stabilizing a strain-temperature response for a shape memory alloy, comprising:
    selecting a first sample of said shape memory alloy for isobaric treatment and a second sample of said shape memory alloy for isothermal treatment, in order to train said shape memory alloy;
    when applying the isobaric treatment to the first sample, applying a constant stress to the first sample and cycling a temperature from a minimum temperature to a maximum temperature until a strain on the first sample stabilizes; and
    when applying the isothermal treatment to the second sample,
    applying different levels of stress on the second sample until a strain on the second sample matches the stabilized strain on the first sample.

2. The method of claim 1, further comprising:
    when applying the isobaric treatment to the first sample, determining whether the constant stress applied to the first sample is based on tension, compression, torsion, or any combination thereof.

3. The method of claim 1, wherein
    the constant stress is based on a size of the first sample and an intended service condition, and
    the minimum temperature and the maximum temperature are based on the intended service condition.

4. The method of claim 1, further comprising:
    when applying the isobaric treatment to the first sample, determining after each cycle whether the strain on the first sample is stabilized in martensite and austenite states.

5. The method of claim 1, further comprising:
    when applying the isothermal treatment to the second sample, determining a stress value having a corresponding strain that matches the stabilized strain of the first sample.

6. The method of claim 5, further comprising:
    selecting an object comprised of said shape memory alloy which is to be trained using an isothermal treatment; and
    when applying the isothermal treatment to the object, applying a stress value on the object to achieve a strain on the object equivalent to the stabilized strain observed in the isobaric condition, wherein the applied stress value is equivalent to the determined stress value from the isothermal treatment of the second sample.

7. The method of claim 6, wherein the temperature under the isothermal treatment is set to a constant.

8. The method of claim 7, wherein the first sample, the second sample and the object comprise the same compound, the compound is Ag—Cd, Au—Cd, Cu—Al—Ni, Cu—Sn, Cu—Zn, Fe—Pt, Mn—Cu, Fe—Mn—Si, a Pt alloy, Co—Ni—Al, Co—Ni—Ga, Ni—Fe—Ga, Ti—Pd, Ni—Ti, Ni—Ti—X, or Ni—Mn—Ga, wherein X is platinum, palladium, gold, hafnium or combinations thereof.

9. A method of stabilizing a strain-temperature response for a shape memory alloy, comprising:
- selecting a first sample of the shape memory alloy for isobaric treatment and a second sample of a shape memory alloy for isothermal treatment, in order to train and stabilize the shape memory alloy against the isobaric condition;
- when applying the isobaric treatment to the first sample,
  - applying a constant stress to the first sample and cycling a temperature from a minimum temperature to a maximum temperature until a strain within the first sample stabilizes; and
- when applying the isothermal treatment to the second sample,
  - applying a stress to the second sample until the second sample fails,
  - measuring each strain within the second sample according to different levels of stress applied on the second sample, and
  - from the measured strains, matching a strain of the second sample with the stabilized strain of the first sample.

10. The method of claim 9, further comprising:
when applying the isobaric treatment to the first sample, determining whether the constant stress applied to the first sample is based on tension, compression, torsion, or any combination thereof.

11. The method of claim 9, wherein
the constant stress is based on a size of the first sample and an intended service condition, and
the minimum temperature and the maximum temperature are based on the intended service condition.

12. The method of claim 9, further comprising:
when applying the isobaric treatment to the first sample, determining after each cycle whether the strain on the first sample is stabilized in martensite and austenite states.

13. The method of claim 9, further comprising:
when applying the isothermal treatment to the second sample, determining a stress value that corresponds to the matched strain of the second sample.

14. The method of claim 13, further comprising:
selecting an object comprised of said shape memory alloy which is to be trained using an isothermal treatment; and
when applying the isothermal treatment to the object, applying a stress value on the object to achieve a stabilized strain on the object equivalent to the stabilized strain observed in the isobaric treatment,
wherein the applied stress value is equivalent to the determined stress value from the isothermal treatment of the second sample.

\* \* \* \* \*